(12) United States Patent
Ofek et al.

(10) Patent No.: US 7,520,858 B2
(45) Date of Patent: Apr. 21, 2009

(54) CATHETER WITH PRESSURE SENSOR AND GUIDANCE SYSTEM

(75) Inventors: Eran Ofek, Modi'in (IL); Douglas P. Zipes, Carmel, IN (US)

(73) Assignee: Physical Logic AG, Zug (CH)

( * ) Notice: Subject to any disclaimer, the term of this patent is extended or adjusted under 35 U.S.C. 154(b) by 0 days.

(21) Appl. No.: 11/757,653

(22) Filed: Jun. 4, 2007

(65) Prior Publication Data

US 2007/0282211 A1 Dec. 6, 2007

Related U.S. Application Data

(60) Provisional application No. 60/803,909, filed on Jun. 5, 2006.

(51) Int. Cl.
*A61B 5/00* (2006.01)

(52) U.S. Cl. .................................................. 600/486
(58) Field of Classification Search ................... None
See application file for complete search history.

(56) References Cited

U.S. PATENT DOCUMENTS

| 4,815,471 | A  | 3/1989 | Stobie |
| 6,264,611 | B1 | 7/2001 | Ishikawa et al. |
| 6,264,612 | B1 | 7/2001 | McConnell et al. |

OTHER PUBLICATIONS translation of JP 06-190050.*

* cited by examiner

*Primary Examiner*—Robert L Nasser
(74) *Attorney, Agent, or Firm*—Edward S. Sherman

(57) ABSTRACT

A catheter terminates at a tip that includes an array of pressure sensors. The sensors are responsive to detect and alert the user to variations of pressure that indicate the tip is either encountering an obstruction or constriction of smaller diameter than the catheter, as well as to guide the catheter through the conduit into which it is being inserted.

12 Claims, 4 Drawing Sheets

CATHETER WITH PRESSURE SENSOR AND GUIDANCE SYSTEM

CROSS REFERENCE TO RELATED APPLICATIONS

The present application claims priority to the U.S. Provisional Patent Application filed on Jun. 5, 2006, titled "Catheter with Pressure Sensor and Guidance System" and having Ser. No. 60/803,909, which is incorporated herein by reference.

BACKGROUND OF INVENTION

The present invention relates to catheters used in invasive medical procedures, and in particular to catheters with a capability to measure pressure.

Catheters are extensively used in medical procedures to probe or open restricted vascular structures or other bodily conduits, in for example the delivery of contrast dyes for radiographic procedures, balloon angioplasty to open coronary or other arteries, delivery of stents, insertion of heart monitors and ECD leads as well as numerous other procedures on humans and other living creatures.

In such catheterization procedures, it is essential that the physician visualize the location of the catheter in the body with respect to the critical tissues and other biological structures. This is usually accomplished by providing an x-ray source and an an X-ray imaging camera equipment are on opposite sides of the patient's body. The X-ray source and camera are under motorized control to precess about the patient so that images can be quickly taken from multiple different angles. Usually at least the tip of catheter is radioopaque, typically comprising a stable barium compound as a filler. During vascular catheterization periodic and repeated injection of X-ray contrast dye from the catheter is required to visualize the blood flow around the catheter, and hence the location of the catheter tip within the arteries or veins. As the contrast agent diffuses into capillaries, it again becomes difficult to visualize the position of the catheter tip.

However, difficulties arise as the catheter technology has improved to where it is possible to probe smaller and smaller conduits or channels. However it is also easier to damage thinner tissue. Further, in arterial catheterization, as less contrast is available in thinner arteries, more contrast agent is required. In these procedures, both the physician, who is close to the patient to guide the catheter, and the patient are exposed to X-rays during the entire procedure. Although the patient receives more X-radiation during a single procedure, the skilled clinician can receive significant accumulated dose from multiple procedures.

Such catheter devices typically include a pressure sensing means at the tip to determine the local blood pressure to confirm that the device is itself is not blocking the artery being probed.

It is therefore an object of the present invention to provide an improved method for guiding catheters without the risk of damage to tissue structures.

It is also an object of the invention to provide means for catheterization that use either a lower x-ray dose and/or a smaller quantity of contrast dye.

SUMMARY OF INVENTION

In the present invention, the first object is achieved by providing a flexible catheter comprising: a smooth elongated tube having a tip, a plurality of pressure sensors distributed about the tip for measuring at least one of pressure fluctuations and variations of pressure associated with the orientation of the catheter within a narrow channel comparable to the width of said smooth elongated tube.

A second aspect of the invention is characterized by the process for inserting a catheter within a narrow channel or body conduit, the process comprising the steps of: providing a catheter according to the first embodiment described above, introducing catheter into a bodily conduit of living creature, selecting a pressure threshold at which one or more the pressure sensors or a measured difference in pressure is responsive to transmit an alarm signal to the user that the catheter should not be advanced further within the living creature.

The above and other aspects of the invention help the physician avoid damage during vascular and other catheterization procedures as well as provide an alternative and complimentary means for detecting obstructions and blockages to radiography.

The above and other objects, effects, features, and advantages of the present invention will become more apparent from the following description of the embodiments thereof taken in conjunction with the accompanying drawings.

DETAILED DESCRIPTION

Figure 1A:
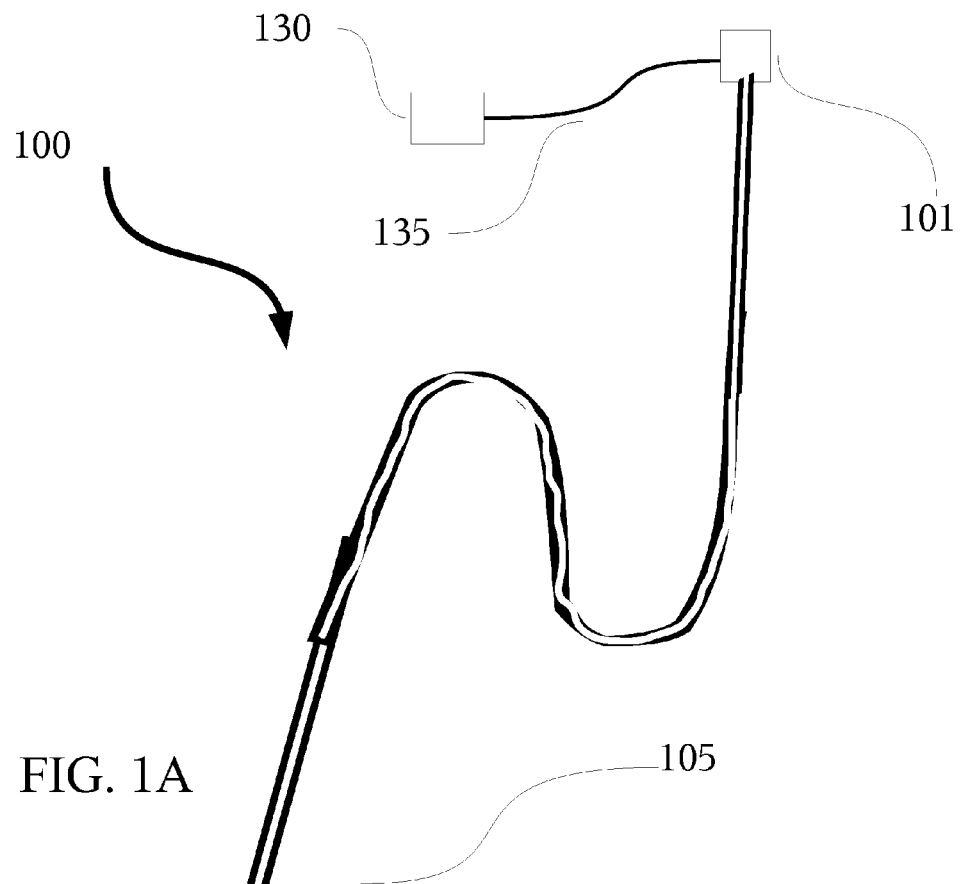
FIG. 1A is a schematic illustration of a catheter device according to an embodiment of the invention.
Figure 1B:
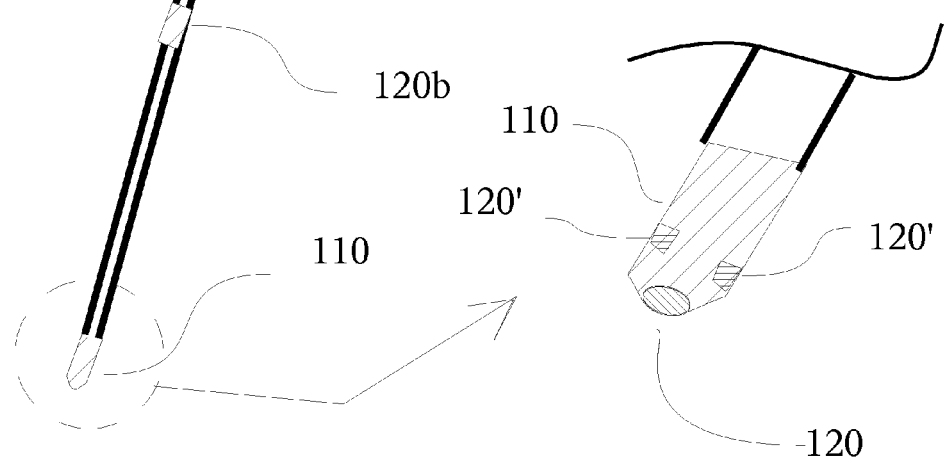
FIG. 1B is a partial view of the tip of the catheter in FIG. 1A.

Referring to FIGS. 1 through 4 wherein like reference numerals refer to like components in the various views, there is illustrated therein a new and improved catheter with pressure sensor and guidance system, generally denominated 100 herein.

FIG. 1A illustrates such a catheter device 100 that comprises an elongated tube 105 that is at least partially flexible, and in particular most flexible wherein it terminates at a tip 110. A plurality of pressure sensors 120' are distributed about the tip 110, one 120 being preferably at the apex of tip 110 as shown in the enlarged partial view in FIG. 1B. Additional sensors, preferably pressure sensors such as 120b, may be disturbed elsewhere along the elongated tube 105 distal from the tip 110 and closer to the conventional control means 101. The elongated tube 105 is at least partially flexible and preferably hollow, having an inner tubular cavity 103 (shown in FIG. 2A) The inner tubular cavity 103 may be used to deliver special probes, fluids or guide wire 107 (shown in FIG. 3A), as well as discrete medical devices or other test instrumentation as is generally known in the art or may be developed at some future time.

Figure 2A:
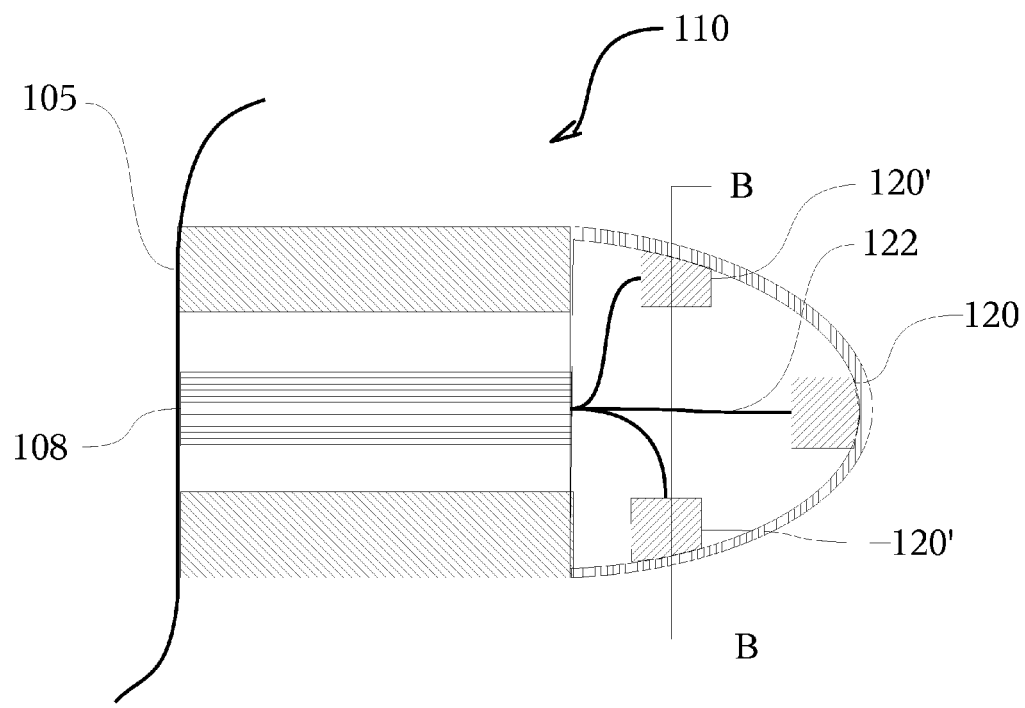
FIG. 2A is a longitudinal sectional elevation through the tip of the catheter of FIG. 1
Figure 2B:
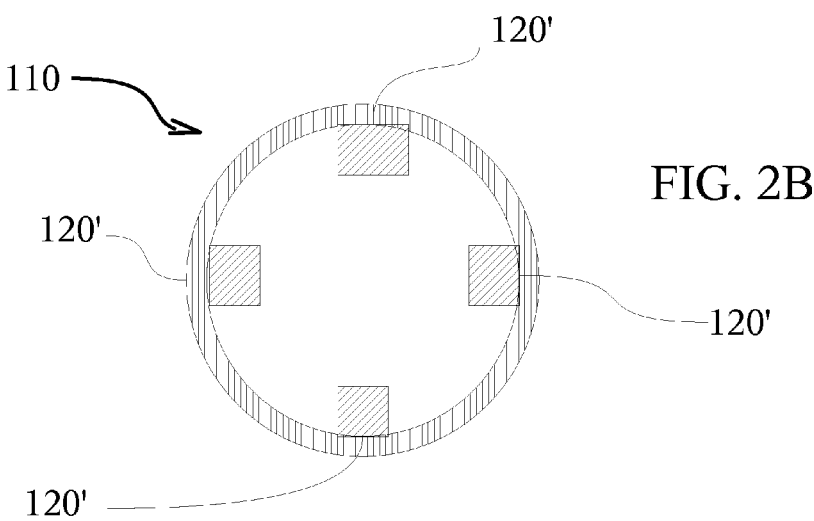
FIG. 2B is a transverse sectional elevation through the tip of the catheter of FIG. 1 at reference line B-B in FIG. 2A.

FIGS. 2A and 2B show the structure of the sensors in tip 110 in more detail. As seen in the longitudinal sectional elevations in FIG. 2A, a first pressure sensor 120 is deployed at the apex of tip 110. A plurality of additional pressure sensors 120' are distributed about the hemispherical portion of the catheter tip 110. For example, sensors 120', as shown in the transverse sectional elevation of FIG. 2B (taken at section reference line B-B in FIG. 2A) are preferably arrayed at equal angular spacing at the periphery of the tip region 110. It should be appreciated that other embodiments include arraying the pressure sensors 120 similarly but on other portions of the catheter distal from tip 110.

Each of the sensors 120 and 120' is connected by wire 122 to a transmitting means. In FIG. 2A the transmitting means is a multi-strand cable 108 or signal cable sending multiplexed or digital signal of the output from all sensors 120 to control unit 101 or via link 135 to monitor or data logger 130, which may include means for signal analysis and processing as will be further described below. The communication link 135 between control means 101 and monitor or data logging means 130 is indicated in FIG. 1A.

Figure 3A:
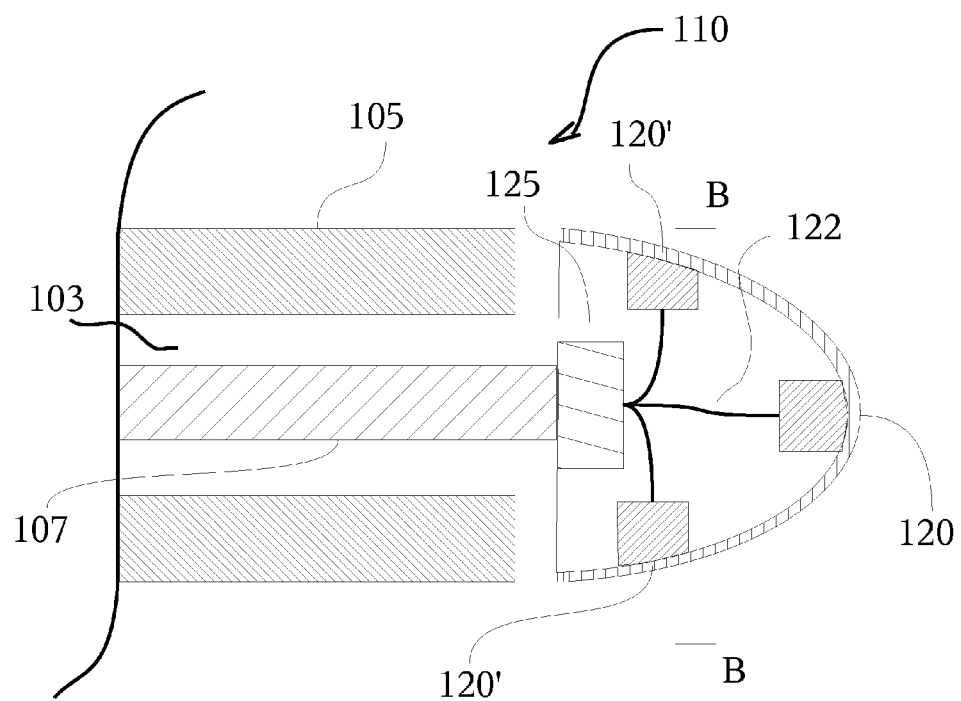
FIG. 3A is a longitudinal sectional elevation through the tip of a catheter according to another embodiment of the invention.
Figure 3B:
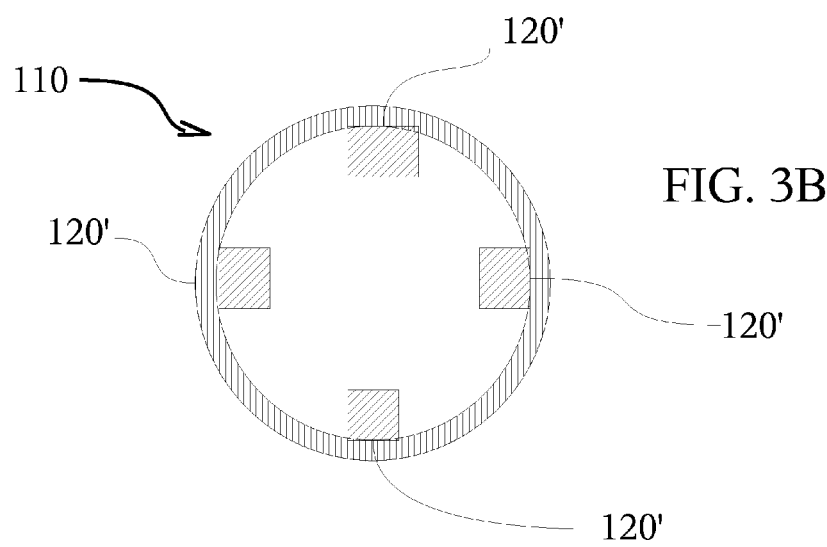
FIG. 3B is a transverse sectional elevation through the tip of the catheter of at reference line B-B in FIG. 3A.

FIGS. 3A and 3B show an alternative embodiment of the invention. As shown in the longitudinal cross sectional elevation of FIG. 3A, the tip 110 with attached or integrated pressure sensors 120 and 120' may extends from tube 105 via guide wire 107 that is disposed in hollow cavity 103. Guide wire 107 may include means for signal wire transmission, or as intended to be illustrated in this non-limiting embodiment an alternative embodiment shown in FIG. 3A the transmitting means is a wireless transmitter 125, such as an RF transmitter. Such an embodiment eliminates the need to deploy a signal cable in cavity 103. Each pressure sensor 120 or 120' is connected to wireless transmitter 125 by signal wire 122. Alternative, the pressure sensor may include an integrated wireless transmitter on the same chip or circuit board, eliminating the need for discrete wire connections.

Figure 4A:
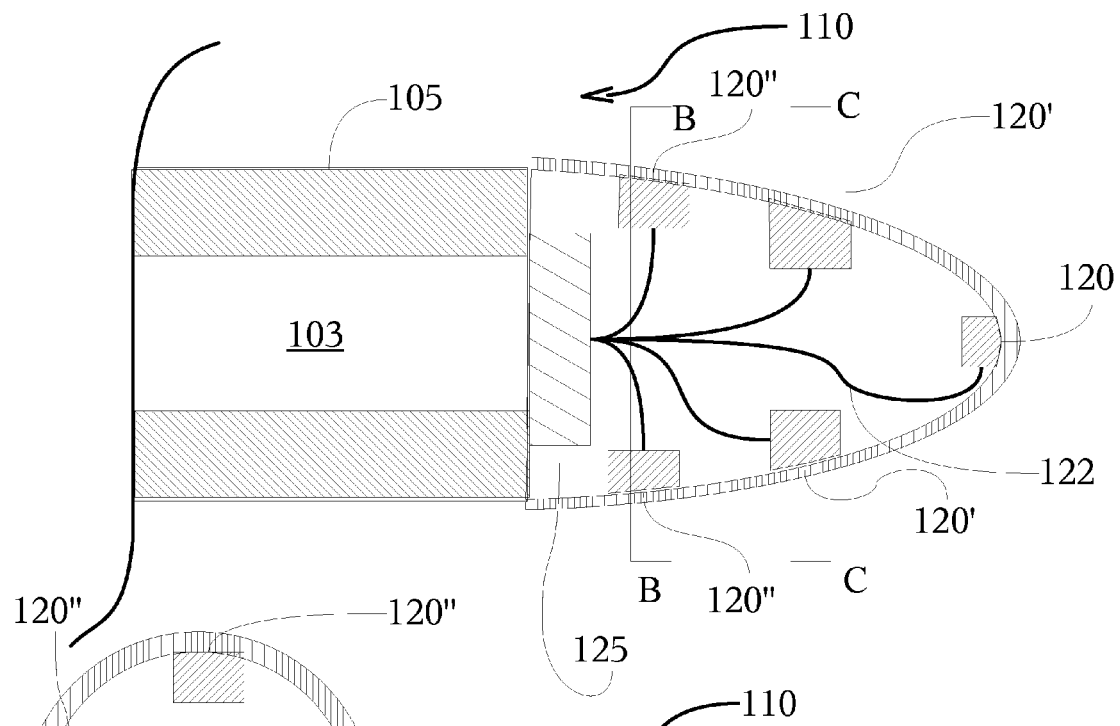
FIG. 4A is a longitudinal sectional elevation through the tip of the catheter of another embodiment of the invention.
Figure 4B:
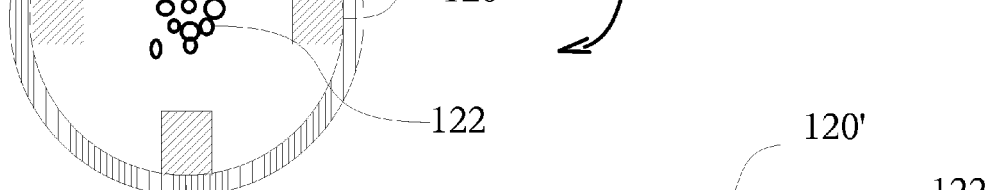
FIG. 4B is a transverse sectional elevation through the tip of the catheter of at reference line B-B in FIG. 4A.
Figure 4C:
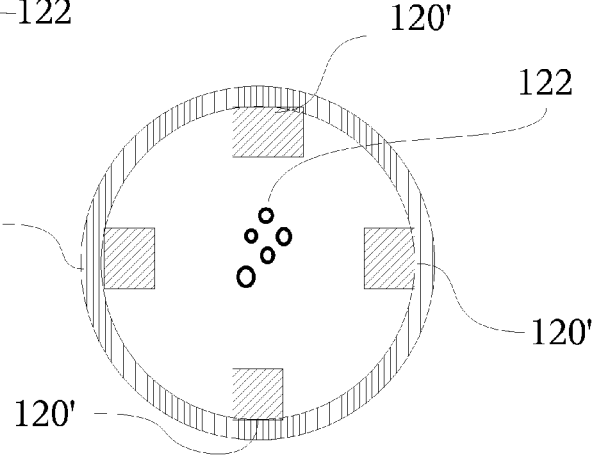
FIG. 4C is a transverse sectional elevation through the tip of the catheter of at reference line C-C in FIG. 4A.

FIGS. 4A and 4B show an alternative embodiment of the invention in which a plurality of sensor arrays are disposed about tip region 110. A first array of pressure sensors 120' is deployed at section C-C located most adjacent to the apex of the tip, which preferably also terminates with a pressure sensor 120. As in the other embodiments, these sensors 120' are preferably arrayed at equal angular spacing at the periphery of the tip region 110. A second array of pressure sensors 120" is deployed a section B-B located from the apex of the tip. As in the other embodiments, these sensors 120 are preferably arrayed at equal angular spacing at the periphery of the tip region 110.

The method of using the catheters of FIG. 1-4 includes determining the difference in force or pressure among the sensors 120 distributed about the tip 110. It is expected that when the tip 110 is centered within an artery or other body tissue conduit, the difference between the pressures measured at each sensor will be at a minimum. However, as the apex of tip 110 steers toward or into an arterial wall or other dense tissue a difference of pressure is expected. As it is preferable that the tip material be compliant to transmit force, displacement or vibrations to the adjacent and attached pressure sensors 120,120' or 120", it is expected that the pressure sensor reading will increase when the tip 110 actually touches the arterial wall. Thus, it is expected that the continuous monitoring of the pressure differences between sensors may be used to steer or guide the catheter down the center of an artery or other tubular tissue structure.

It is a further embodiment of the invention that the monitor or data logging means 130 preferably includes provisions for setting a pressure threshold that signals an alarm or alert to the physician indicating the tip 110 of catheter 100 is either misguided from the center of the conduit or is close to a breaching or tearing tissue that it touches. This will permit the physician to withdraw or redirect the catheter tip 110 before such damage occurs.

Preferably, sensors 120 are nano-sized or MEMS transducers, such as those disclosed in currently pending patent applications, which are listed in Appendixes 1-4 of the US Provisional Patent Application from which this application depends, being incorporated herein by reference. It should be understood that depending on the compliance and damping characteristics of the preferably compliant material that forms tip 110 and supports or surrounds sensors 120, 120' and 120", the term pressure sensor means a mechanical transducer that detects at least one of variations in force, displacement or vibration.

While the invention has been described in connection with a preferred embodiment, it is not intended to limit the scope of the invention to the particular form set forth, but on the contrary, it is intended to cover such alternatives, modifications, and equivalents as may be within the spirit and scope of the invention as defined by the appended claims.

The invention claimed is:

1. A process for inserting a catheter within a narrow channel, the process comprising the steps of:
   a) providing a catheter comprising
      i) a smooth elongated tube having a tip,
      ii) a plurality of pressure sensors distributed about the tip for measuring at least one of pressure fluctuations and variations of pressure associated with the orientation of the catheter within a narrow channel comparable to the width of said smooth elongated tube,
   b) introducing the catheter into a bodily conduit of living creature,
   c) monitoring at least one of the absolute and differential pressure between the plurality of sensors,
   d) transmitting to the user instructions to steer the catheter based on the difference in pressure between two or more of the sensors in the plurality of sensors.

2. A process for inserting a catheter according to claim 1 further comprising the step of selecting a pressure threshold at which one or more the pressure sensors is responsive to transmit an alarm signal to the user that the catheter should not be advanced further within the living creature.

3. A process according to claim 1 wherein at least one pressure sensor is disposed at the tip of the catheter.

4. A process according to claim 1 wherein the tip of the catheter is more compliant than the smooth elongated tube so as to transmit energy to the pressure sensors.

5. A process according to claim 1 wherein two or more pressure sensors are disposed at substantially equal radial spacing around the circumference of the tip of the catheter.

6. A process for inserting a catheter according to claim 1 wherein a least one of said plurality of pressure sensors of the catheter is a MEMS sensor.

7. A process for inserting a catheter according to claim 1 wherein a least one of said plurality of pressure sensors of the catheter is a nano sensor comprising:
   a) non-rigid substrate,
   b) a non-conductive columnar spacer disposed on said non-rigid substrate,
   c) an array of particles bonded to said substrate via said spacer wherein at least one column is connected to each particle, d) whereby deformation of said non-rigid substrates results in a perturbation to the distribution of the particles in said array to produce a measure change in the aggregate physical property of said array.

8. A process for inserting a catheter according to claim 1 wherein a least one of said plurality of pressure sensors of the catheter is a nano sensor comprising:
   a) a substrate,
   b) a polymeric spacer layer disposed on said substrate,
   c) an array of particles bonded to the surface of said polymeric spacer,
   d) whereby deformation of at least one of said substrate and said polymeric spacer layer results in a perturbation to the distribution of the nano-particles in said array to produce a measurable change in the aggregate physical property of said array.

9. A process for inserting a catheter according to claim 8 wherein a least one of said plurality of pressure sensors of the catheter is a nano sensor comprising conductive nanoparticles and the property is electrical resistance.

10. A process for inserting a catheter according to claim 1 wherein a least one of said plurality of pressure sensors of the catheter is a nano sensor comprising:
   a) a substrate,
   b) a supporting plate extending upward from said substrate,
   c) a beam coupled on at least one end to said supporting plate and extending over said substrate,
   d) a strain sensitive conductive coating disposed on at least one surface of said beam that extends over said substrate,
   e) a pair of electrodes disposed in electrical contact to said strain sensitive coating to measure a change in resistance there between in response to the deformation of the portion of said beam that extends over substrate.
   f) wherein said strain sensitive coating comprises a 2-dimensional array of substantially mono-disperse conductive nanoparticles mechanically coupled to said beam wherein the nanoparticles in said array separate from each other in response to the deformation of said beam.

11. A process for inserting a catheter according to claim 1 wherein a least one of said plurality of pressure sensors of the catheter is a nano sensor comprising:
   a) a plurality of repeating thin film layers having in a repeating sequence the ordered structure of:
   i) a dielectric material,
   ii) a first conductive layer,
   iii) a dielectric material,
   iv) a second conductive layer, wherein when the first and second layers are metals, the work function of the first metal differs from the work function of the second metal, and when the first and second layers are semiconductors the Fermi level of the first semi-conductor differs from the Fermi level of the second semi-conductor, and
   b) a first terminal connecting all the first conductive layers,
   c) a second terminal connecting all the second conductive layers, wherein the first and second conductive layers are electrically insolated by the dielectric materials.

12. A process for inserting a catheter according to claim 11 wherein a least one of said plurality of pressure sensors of the catheter is a nano sensor
   wherein at least one of the first and second conductive layers is a metal and at least one of the dielectric materials is polymeric.

\* \* \* \* \*